US012759890B2

(12) United States Patent
Tinge et al.

(10) Patent No.: US 12,759,890 B2
(45) Date of Patent: Oct. 13, 2026

(54) AMMONIUM SULPHATE PRODUCTION ON INDUSTRIAL SCALE

(71) Applicant: CAP III B.V., EL Urmond (NL)

(72) Inventors: Johan Thomas Tinge, EL Urmond (NL); Jarno Martijn Westerhof, EL Urmond (NL); Olaf Poorter, EL Urmond (NL)

(73) Assignee: CAP III B.V., El Urmond (NL)

( * ) Notice: Subject to any disclaimer, the term of this patent is extended or adjusted under 35 U.S.C. 154(b) by 894 days.

(21) Appl. No.: 17/796,631

(22) PCT Filed: Feb. 4, 2021

(86) PCT No.: PCT/EP2021/052670
§ 371 (c)(1),
(2) Date: Jul. 29, 2022

(87) PCT Pub. No.: WO2021/156371
PCT Pub. Date: Aug. 12, 2021

(65) Prior Publication Data

US 2023/0054797 A1 Feb. 23, 2023

(30) Foreign Application Priority Data

Feb. 7, 2020 (EP) .................................... 20156175

(51) Int. Cl.
*C01C 1/242* (2006.01)
*C07D 201/06* (2006.01)
*C07D 201/16* (2006.01)

(52) U.S. Cl.
CPC ............ *C01C 1/242* (2013.01); *C07D 201/06* (2013.01); *C07D 201/16* (2013.01)

(58) Field of Classification Search
None
See application file for complete search history.

(56) References Cited

U.S. PATENT DOCUMENTS 3,530,924 A 9/1970 Domning et al.
4,015,946 A 4/1977 Bonnema et al.
(Continued)

FOREIGN PATENT DOCUMENTS

CN 1378522 A 11/2002
CN 1566089 A 1/2005
(Continued)

OTHER PUBLICATIONS

Mitsuru et al. JP 2010-163319 A1, Machine-generated English translation.*
(Continued)

*Primary Examiner* — Yun Qian
(74) *Attorney, Agent, or Firm* — Honigman LLP; Andrew N. Weber; Jonathan P. O'Brien

(57) ABSTRACT

The invention provides a process for the production of crystalline ammonium sulfate, wherein the process comprises performing a Beckmann rearrangement reaction, neutralizing the Beckmann rearrangement reaction mixture, separating a first aqueous ammonium sulfate phase and an aqueous ε-caprolactam phase, charging the first ammonium sulfate phase to a first evaporative type crystallization section wherein crystalline ammonium sulfate is obtained, discharging from the first evaporative type crystallization section mother liquor enriched in organic components, extracting the aqueous ε-caprolactam phase to obtain an extracted ε-caprolactam phase and a second aqueous ammonium sulfate phase, discharging the mother liquor that is discharged from the first evaporative type crystallization section and/or the second aqueous ammonium sulfate phase to a second evaporative type crystallization section wherein evaporative type crystallization is performed so that a three-phase system occurs. At least a liquid oily phase is recovered from the three-phase system. The invention further provides
(Continued)

a plant suitable to carry out the process of the invention, crystalline ammonium sulfate and a liquid oily phase obtained by the process of the invention.

11 Claims, 3 Drawing Sheets

(56) References Cited

U.S. PATENT DOCUMENTS

| | | | |
|---|---|---|---|
| 9,908,785 | B2 | 3/2018 | Tinge et al. |
| 2011/0038781 | A1 | 2/2011 | Hoffman et al. |
| 2015/0218008 | A1 | 8/2015 | Ekkelenkamp |
| 2016/0159657 | A1 | 6/2016 | Tinge et al. |

FOREIGN PATENT DOCUMENTS

| | | | |
|---|---|---|---|
| CN | 1757599 | A | 4/2006 |
| CN | 101070299 | A | 11/2007 |
| CN | 103864689 | A | 6/2014 |
| CN | 105408313 | A | 3/2016 |
| CN | 105439174 | A | 3/2016 |
| CN | 103864689 | | 12/2017 |
| EP | 1206411 | | 10/2007 |
| GB | 748572 | | 5/1956 |
| JP | 532490 | A | 1/1978 |
| JP | 54128589 | | 10/1979 |
| JP | 02279514 | A | 11/1990 |
| JP | 03150217 | A | 6/1991 |
| JP | 03247507 | A | 11/1991 |
| JP | 06219731 | A | 8/1994 |
| JP | 2010-163319 | | 7/2010 |
| JP | 2016505580 | A | 6/2014 |
| PL | 210210 | B1 | 12/2011 |
| RU | 2325324 | C2 | 1/2008 |
| RU | 2427570 | C2 | 11/2008 |
| SU | 1446108 | A1 | 12/1988 |
| WO | 2000066561 | A1 | 11/2000 |
| WO | 112549 | A | 2/2001 |
| WO | 2014/206869 | | 12/2014 |
| WO | 2015/010885 | | 1/2015 |
| WO | 2021/094184 | | 5/2021 |
| WO | 2021/156371 | | 8/2021 |

OTHER PUBLICATIONS

Search Report issued by the Taiwanese Patent Office dated Sep. 10, 2024 for Application 110104273.
Office Action, CN Application 202180012724.6, dated Jul. 20, 2023.
Office Action, JP Application 2022547812, dated Jan. 30, 2025.
International Search Report for PCT/EP2014/062987 mailed Oct. 21, 2014.
International Search Report for PCT/EP2021/052670 mailed Apr. 23, 2021.
Kawakami, Tadao, "Industrial application of nonaqueous solution chemistry", Chemical Engineering, vol. 23, No. 2, 1959, p. 45.
International Search Report for PCT/EP2020/081077 mailed May 20, 2021.
Office Action, IN Application No. 202217043926, dated Oct. 6, 2025.
Decision about Grant, BY Application No. 20220215, dated Aug. 22, 2025.

* cited by examiner

AMMONIUM SULPHATE PRODUCTION ON INDUSTRIAL SCALE

CROSS REFERENCE TO RELATED APPLICATION

This U.S. nonprovisional application is the 35 USC § 371 national phase of PCT Application No. PCT/EP2021/052670, filed on Feb. 4, 2021, which claims the benefit of EP Application Serial No. 20156175.0, filed on Feb. 7, 2020. Each of these documents is hereby incorporated by reference in its entirety.

TECHNICAL FIELD OF THE INVENTION

The invention relates to an industrial scale continuous process for producing crystalline ammonium sulfate from aqueous streams comprising organic components whereby said streams originate from an ε-caprolactam production process.

BACKGROUND OF THE INVENTION

Ammonium sulfate is valuable as a fertilizer providing nitrogen and sulfur, e.g., for use in agriculture, horticulture or forestry and is for this type of use often applied as a crystalline material. For the ease of use as a fertilizer, the size distribution of the ammonium sulfate crystals plays a critical role. In general, large crystals are desired by the fertilizer industry and easier to handle. Crystals with a relatively large average crystal size can be used in commercially valuable fertilizer blends and are therefore economically more valuable than smaller crystals. Ammonium sulfate crystals usually contain various organic and inorganic impurities originating from the various types of streams or feed stocks that are used for their production.

ε-caprolactam is an important organic chemical raw material used inter alia in the production of polyamide 6 (also called nylon 6). It can be prepared by subjecting cyclohexanone oxime to the Beckmann rearrangement reaction in the presence of sulfuric acid and/or oleum (see, e.g., Ullmann's Encyclopedia of Industrial Chemistry (2018) Chapter 'Caprolactam'; https://doi.org/10.1002/14356007.a05_031.pub3). Oleum is a mixture of sulfuric acid and $SO_3$, which acts as a catalyst for the conversion of cyclohexanone oxime towards ε-caprolactam. After the rearrangement reaction, a base, usually ammonia, is added to the Beckmann rearrangement mixture to produce a neutralized Beckmann rearrangement mixture. The neutralized Beckmann rearrangement mixture typically comprises an aqueous ammonium sulfate phase (called "first aqueous ammonium sulfate phase" herein) and an aqueous ε-caprolactam phase. The first aqueous ammonium sulfate phase still contains some ε-caprolactam and the aqueous ε-caprolactam phase still contains some ammonium sulfate. Additionally, both phases comprise unwanted organic components, i.e., impurities. Such unwanted organic components are, e.g., cyclohexanone oxime, cyclohexanone, 2-cyclohexen-1-one, 2-hydroxycyclohexan-1-one, 1,2-cyclohexanedione, and 1,2,3,4,6,7,8,9-octahydrophenazine (see, e.g., Du et al. "Impurity formation in the Beckmann rearrangement of cyclohexanone oxime to yield ε-caprolactam" *Industrial & Engineering Chemistry Research* 56, 48 (2017), pp. 14207-14213).

The first aqueous ammonium sulfate phase is usually extracted with an organic solvent to remove residual amounts of ε-caprolactam. From the thus-obtained largely ε-caprolactam-free first aqueous ammonium sulfate phase, the organic solvent is usually recovered. First aqueous ammonium sulfate phases that are co-produced in ε-caprolactam production processes often contain more than 50 wt. % water and less than 50 wt. % ammonium sulfate. Additionally, such phases contain unwanted organic components from the Beckmann rearrangement reaction.

The aqueous ε-caprolactam phase can also be extracted with an organic solvent, whereby an organic, ε-caprolactam containing phase and another aqueous ammonium sulfate phase (called "second aqueous ammonium sulfate phase" herein) are formed. Pure ε-caprolactam is recovered from the organic ε-caprolactam containing phase by a series of purification and concentration steps. From the second aqueous ammonium sulfate phase remaining traces of organic solvent are usually recovered. Also this second aqueous ammonium sulfate phase contains unwanted organic components from the Beckmann rearrangement reaction.

Both of the above-described first and second aqueous ammonium sulfate phases cannot be simply disposed of because they both contain organic components that would pollute the environment. The treatment of these two phases in a wastewater treatment plant, however, is very costly due to the high concentration of both ammonia and organic components contained therein.

The organic components contained in the first and second aqueous ammonium sulfate phases obtained from the neutralized Beckmann rearrangement mixture make it difficult to produce pure crystalline ammonium sulfate by evaporative crystallization therefrom. During evaporative crystallization, the organic components become concentrated in the aqueous phase and easily incorporate into the forming ammonium sulfate crystals. To reduce the incorporation of organic components in the ammonium sulfate crystals, usually a purge is performed, whereby mother liquor, i.e., an aqueous ammonium sulfate phase enriched in organic components, is, continuously or periodically, discharged from the evaporative type crystallization section. Due to the fact that these/this purge(s) contain(s) organic components, they cannot be disposed as such. As a consequence, cost-intensive treatments of these purges in a wastewater treatment plant are necessary. Moreover, a further disadvantage of the purging from the evaporative type crystallization section is that also valuable ammonium sulfate is removed. This reduces the overall yield of ammonium sulfate crystals obtainable from the two aqueous ammonium sulfate phases of the neutralized Beckmann rearrangement mixture. Thus, the purging has a negative impact on the economics of ammonium sulfate crystal production from a neutralized Beckmann rearrangement mixture.

Already for a long period of time, there has been a need to implement a process for treating the first and second aqueous ammonium sulfate phases comprising organic components, obtained from a neutralized Beckmann rearrangement mixture, in an economic and an ecologically (eco-) friendly manner.

CN 1 023 790 describes a process for treating an ammonium sulfate solution phase of a neutralized Beckmann rearrangement mixture. Ammonium sulfate crystals are recovered from the ammonium sulfate solution phase, and organic components originating from the ammonium sulfate solution phase are oxidized in a wet air oxidation process. Ammonium sulfate crystals are recovered from the ammonium sulfate solution phase using a crystallizer which is operated by evaporation. Mother liquor which contains organic components is removed from the crystallizer and treated in a wet air oxidation process. In the wet air oxidation process, the mother liquor is contacted with an oxygen-containing gas in a wet air oxidation reactor, resulting in gaseous oxidized products and purified ammonium sulfate solution. The purified ammonium sulfate solution which has a decreased amount of organic components is recycled to the crystallizer. CN 1 023 790 does not disclose a treatment of the eluate phase containing ammonium sulfate which is formed by extracting the aqueous ε-caprolactam phase of the neutralized Beckmann rearrangement mixture with an organic solvent. Thus, CN 1 023 790 does not solve the disposal problem for both types of aqueous ammonium sulfate phases obtainable from the neutralized Beckmann rearrangement mixture. Moreover, CN 1 023 790 does not disclose how to produce high grade crystalline ammonium sulfate from aqueous phases containing ammonium sulfate and organic components.

JP 4 903 271 6 discloses a process for treating a neutralized Beckmann rearrangement mixture. After separation of the ε-caprolactam phase, the aqueous ammonium sulfate solution is heat-treated at from 150 to 350° C. under increased pressure in oxygen or gas which contains oxygen. The process of JP 4 903 271 6 does not disclose a treatment of the aqueous eluate phase containing ammonium sulfate which is formed by extracting the ε-caprolactam phase of the neutralized Beckmann rearrangement mixture with an organic solvent. Thus, also JP 4 903 271 6 does not solve the disposal problem for both types of aqueous ammonium sulfate phases obtainable from the neutralized Beckmann rearrangement mixture. Moreover, JP 4 903 271 6 does not disclose how to produce high grade crystalline ammonium sulfate from aqueous phases containing ammonium sulfate and organic components.

EP 1 206 411 B1 discloses a process for treating a mixture, in particular a neutralized Beckmann rearrangement mixture, comprising i) an ammonium sulfate solution phase containing first organic components and ii) an aqueous ε-caprolactam phase containing second organic components, wherein said process comprises forming an aqueous liquid containing the first and second organic components, and subjecting the aqueous liquid to a wet air oxidation process to purify the aqueous liquid. EP 1 206 411 B1 does not disclose the production of a liquid oily phase. Moreover, EP 1 206 411 B1 does not disclose how to produce high grade crystalline ammonium sulfate from aqueous phases containing ammonium sulfate and organic components.

The prior art processes often employ a disadvantageous wet air oxidation, a process that requires a combination of high pressures and high temperatures and usually uses pure oxygen as feed stock. The harsh process conditions cause a high consumption of energy so that high process costs arise. In addition, the variable process costs are high, inter alia due to the consumption of pure oxygen. Moreover, the investments and maintenance costs of the plant equipment used for the wet air oxidation technology are very high due to the employed harsh process conditions. Finally, wet air-based technologies do not oxidize all materials completely to carbon dioxide and water. Instead, some intermediate compounds, e.g., carboxylic acids, are formed, which represent about a quarter of the original mass of organic components. For this reason, liquid wastes that are treated by wet air oxidation require additional treatment processes for final clean-up.

SUMMARY OF THE INVENTION

In light of the prior art, the object of the present invention is to provide a process for obtaining and/or treating

- a first aqueous ammonium sulfate phase contaminated with organic components directly obtained from a neutralized Beckmann rearrangement mixture; and
- a second aqueous ammonium sulfate phase contaminated with organic components obtained from the processing of an aqueous ε-caprolactam phase of a neutralized Beckmann rearrangement mixture.

At the same time, the object of the present invention is to provide a process that produces from at least one aqueous ammonium sulfate phase contaminated with organic components high grade ammonium sulfate crystals. Moreover, it is an object of the present invention to provide an eco-friendly process in that reduced amounts of liquid wastes comprising organic components are generated and/or put to another use. It is also an object of the present invention to provide an economically valuable and cost-efficient process.

Overall, the object of the present invention is to provide an economic and eco-friendly process to produce high grade ammonium sulfate from an initial Beckmann rearrangement mixture comprising organic components.

The aforementioned objects are solved by the process, the plant, the crystalline ammonium sulfate and the liquid oily phase described herein.

In a first aspect, the present invention concerns a process for the production of crystalline ammonium sulfate in an industrial scale plant, wherein the plant comprises

- a Beckmann rearrangement reaction section,
- a neutralization section,
- a first liquid-liquid separation section,
- a first and a second extraction section,
- a first solvent recovery section,
- a first and a second evaporative type crystallization section,
- and a first liquid-solid separation section;

wherein the method comprises the steps of:

a) charging components
   (i) sulfuric acid and/or oleum; and
   (ii) cyclohexanone oxime
   to the Beckmann rearrangement reaction section and reacting the same to form a mixture comprising ε-caprolactam;
b) discharging the resulting mixture comprising ε-caprolactam from the Beckmann rearrangement reaction section to the neutralization section;
c) adding ammonia and water to the mixture comprising ε-caprolactam in the neutralization section, whereby a neutralized Beckmann rearrangement mixture is obtained that comprises a first aqueous ammonium sulfate phase and an aqueous ε-caprolactam phase, both of which comprise organic components as impurities;
d) separating the first aqueous ammonium sulfate phase and the aqueous ε-caprolactam phase obtained in the neutralization section in the first liquid-liquid separation section;
e) treating the first aqueous ammonium sulfate phase obtained in step d) by
   e.1) extracting the first aqueous ammonium sulfate phase with a first organic solvent in the first extraction section, whereby a phase comprising first organic solvent and ε-caprolactam, and an extracted first aqueous ammonium sulfate phase are obtained;
   e.2) charging the extracted first aqueous ammonium sulfate phase to the first solvent recovery section, wherein first organic solvent is recovered and a recovered first aqueous ammonium sulfate phase is obtained;

e.3) charging the recovered first aqueous ammonium sulfate phase to the first evaporative type crystallization section and performing evaporative type crystallization therein to obtain crystalline ammonium sulfate and mother liquor in the first evaporative type crystallization section, wherein the mother liquor is an aqueous ammonium sulfate phase enriched in organic components compared to the recovered first aqueous ammonium sulfate phase entering the first evaporative type crystallization section;

e.4) discharging mother liquor from the first evaporative type crystallization section;

e.5) discharging a slurry comprising crystalline ammonium sulfate from the first evaporative type crystallization section and charging it to the first liquid-solid separation section to recover crystalline ammonium sulfate;

f) treating the aqueous ε-caprolactam phase obtained in step d) by f.1) extracting the aqueous ε-caprolactam phase in the second extraction section with a second organic solvent, whereby a phase comprising second organic solvent and ε-caprolactam, and a second aqueous ammonium sulfate phase comprising organic components are obtained;

characterized in that (i) the mother liquor that is discharged from the first evaporative type crystallization section in step e.4) and/or (ii) the second aqueous ammonium sulfate phase comprising organic components that is obtained in step f.1) are/is charged to the second evaporative type crystallization section, wherein evaporative type crystallization is performed so that a three-phase system occurs:

(1) a liquid oily phase comprising organic components;

(2) a crystalline ammonium sulfate phase; and (3) a liquid aqueous ammonium sulfate comprising phase;

(iii) recovering at least the oily phase from said three-phase system.

In the process of the invention, ε-caprolactam is produced by a Beckmann rearrangement reaction whereby cyclohexanone oxime is used as starting material and sulfuric acid and/or oleum serve(s) as catalyst (step a)). The Beckmann rearrangement reaction mixture is subsequently neutralized with ammonia (steps b) and c)), so that a neutralized Beckmann rearrangement reaction mixture is obtained. This neutralized Beckmann rearrangement mixture has two phases, a first aqueous ammonium sulfate phase and an aqueous ε-caprolactam phase, both of which comprise organic components as impurities. Said phases of the neutralized Beckmann rearrangement mixture are separated from each other in step d), whereby both phases are further processed in steps e) and f).

The treatment of the first aqueous ammonium sulfate phase in step e) includes the extraction with a first organic solvent and the recovery of that first solvent, whereby a recovered first aqueous ammonium sulfate phase is obtained, which is charged (steps e.1) and e.2)) to a first evaporative type crystallization section (step e.3)). Evaporative type crystallization is performed in said first evaporative type crystallization section to obtain crystalline ammonium sulfate and mother liquor. A part of the mother liquor is discharged from the first evaporative type crystallization section (step e.4)). The crystalline ammonium sulfate obtained in the first evaporative type crystallization section is discharged as a slurry and charged to a first liquid-solid separation section to recover crystalline ammonium sulfate (step e.5)). Process step e) of the present invention produces high-grade (i.e., pure and large size) crystalline ammonium sulfate.

The treatment of the aqueous ε-caprolactam phase in step f) includes the extraction of the aqueous ε-caprolactam phase in a second extraction section with a second organic solvent (step f.1)). This extraction results in the production of a second aqueous ammonium sulfate phase comprising organic components. In addition, a phase comprising ε-caprolactam and second organic solvent is obtained from which pure ε-caprolactam is recovered.

The process of the invention is characterized in that (i) the mother liquor discharged in step e.4), or (ii) the second aqueous ammonium sulfate phase comprising organic components obtained in step f.1) or both are charged to a second evaporative type crystallization section, wherein evaporative type crystallization is performed so that (i.e., the conditions in the second evaporative type crystallization section are set so that) a three-phase system occurs:

(1) a liquid oily phase comprising organic components;

(2) a crystalline ammonium sulfate phase; and (3) a liquid aqueous ammonium sulfate comprising phase.

At least the liquid oily phase is recovered from the three-phase system. This means that the oily phase is obtained as another product of the process of the invention apart from ammonium sulfate crystals and ε-caprolactam. The liquid oily phase of the process of the invention can advantageously be put to another use as explained further below.

It was surprising that the process of the invention yields high quality ε-caprolactam and high quality crystalline ammonium sulfate, while reducing impurity outlets. This is achieved by implementing recycling loops (i) and/or (ii) as outlined above and performing a second evaporative type crystallization on those recycled streams to produce a liquid oily phase comprising organic impurities.

The generation of the liquid oily phase is an advantage of the present invention. By producing said liquid oily phase, the liquid waste problem is reduced or even eliminated by producing a reduced volume of secondary product in form of a liquid oily phase comprising organic components. This liquid oily phase can be put to another use such as combustion as such or combustion with recovery of heat. The liquid oily phase can be incinerated without the need to add extra fuel. The heat recovered from the combustion can advantageously be used to generate steam. As such, the present invention also provides as a separate product a useful oily phase as defined herein, in particular a liquid oily phase comprising between 0.5 and 25 wt. %, preferably between 1 and 20 wt. %, and more preferably between 2 and 15 wt. % ε-caprolactam; and organic components in an amount of from 500 to 2000 gram COD/kg, preferably 750 to 2000 gram COD/kg and more preferably 1000 to 2000 gram COD/kg of the liquid oily phase.

The present invention also includes the crystalline ammonium sulfate that is produced in the second evaporative type ammonium sulfate crystallization section in the presence of the liquid oily phase.

Unlike the processes of the prior art, the process of the invention does not require any harsh process conditions such as high super-atmospheric pressures (e.g., greater than 2 bar) or temperatures above 120° C. The process of the invention does not require pure oxygen as feed stock. All of this is advantageous because it reduces the energy consumption for executing the process of the invention and also reduces the investments and maintenance costs for the plant equipment required to carry out the process of the invention. Harsh process conditions, however, were common practice in the prior art, in particular during wet air oxidation.

Overall, the process of the invention produces high-quality products in form of ammonium sulfate crystals and ε-caprolactam, and additionally a liquid oily phase. The process of the invention can be operated at low costs due to low energy consumption and the production of reduced amounts of liquid waste comprising organic components that needs to be treated in a waster water treatment plant. This results in an improved overall carbon foot print for the ε-caprolactam and ammonium sulfate production process.

Next to the process of the invention, the present invention also provides an industrial scale plant suitable to carry out the process of the invention. The plant comprises as equipment at least those described for the process of the invention above, namely a Beckmann rearrangement reaction section, a neutralization section, a first liquid-liquid separation section, a first and a second extraction section, a first solvent recovery section, a first and a second evaporative type crystallization section, and a first liquid-solid separation section.

Advantageous embodiments of the invention are indicated in the dependent claims and are explained in more detail in the following.

DETAILED DESCRIPTION OF THE INVENTION

The Process

The process of the invention is conducted in an industrial scale plant which comprises a Beckmann rearrangement reaction section, a neutralization section, a first liquid-liquid separation section, a first and a second extraction section, a first solvent recovery section, a first and a second evaporative type crystallization section, and a first liquid-solid separation section.

The process of the invention is a multi-step process, in which several phases are obtained and processed further. The term "phase" as used herein refers to a distinguishable matter such as a solid, liquid or gas. A liquid phase as used herein can comprise dissolved and/or undissolved organic and/or inorganic components in solvent. An "aqueous phase" as used herein means that the majority of the solvent is water. "Solvent", as used herein, is a liquid in which the "product" (e.g., ε-caprolactam or ammonium sulfate) is at least partially dissolved in. "Solvent" and "product" refer to different entities. For example, the aqueous ε-caprolactam phase may contain 30 wt. % water and 70 wt. % ε-caprolactam. It is called "aqueous" because the majority of the solvent (100% in this example) is water. An "organic phase" as used herein means that the majority of the solvent is an organic solvent.

The phases obtained in the process of the invention differ in the contained components or if not already in the type of the contained components at least in the quantity of the contained components. The ranges indicated in the following for each component of a particular phase, can be combined with any range indicated for another component of the same phase. In particular, the ranges of the same "preference level" are compatible for different components of the same phase.

Step a)

In step a) of the process of the invention, the components sulfuric acid and/or oleum and cyclohexanone oxime are charged to the Beckmann rearrangement reaction section. The cyclohexanone oxime is subjected to a Beckmann rearrangement reaction whereby the sulfuric acid and/or oleum act(s) as catalyst. The Beckmann rearrangement reaction is highly exothermic, and is therefore typically controlled by a cooling system. The reaction mixture produced in the Beckmann rearrangement section comprises ε-caprolactam.

Step b)

In step b) of the process of the invention, the Beckmann rearrangement reaction mixture comprising ε-caprolactam is discharged from the Beckmann rearrangement reaction section to a neutralization section. The term "discharging" as used herein means "removing".

Step c)

Step c) of the process of the invention takes places in the neutralization section. In step c), ammonia and water are added to the Beckmann rearrangement reaction mixture comprising ε-caprolactam. This leads to the formation of a neutralized Beckmann rearrangement mixture. Said neutralized Beckmann rearrangement mixture comprises two phases. One phase is an aqueous ammonium sulfate phase. It is referred to as "the first aqueous ammonium sulfate phase" herein. The second phase is an aqueous ε-caprolactam phase. Both phases of the neutralized Beckmann rearrangement mixture comprise impurities in form of organic components. In addition, both phases can contain inorganic components as impurities. The aqueous ε-caprolactam phase contains in particular ammonium sulfate as inorganic impurity.

The term "organic components" used herein refers to organic compounds that can be oxidized. These oxidizable organic compounds represent unwanted impurities in the phases that comprises them. The type and quantity of organic components can vary in between different phases generated during the process of the invention. For example, the first aqueous ammonium sulfate phase generated in step c) comprises as largest quantitative organic component or impurity ε-caprolactam.

Step d)

In step d) of the process of the invention, the first aqueous ammonium sulfate phase and the aqueous ε-caprolactam phase of the neutralized Beckmann rearrangement mixture are separated from each other in the first liquid-liquid separation section.

In an embodiment of the invention, the first aqueous ammonium sulfate phase of step d) comprises 25 to 50 wt. %, preferable 35 to 48 wt. % and more preferably 39 to 45 wt. % ammonium sulfate.

In another embodiment of the invention, the first aqueous ammonium sulfate phase of step d) comprises as main organic component ε-caprolactam. The first aqueous ammonium sulfate phase can comprise as further organic components cyclohexanone oxime and side-products of the Beckmann rearrangement reaction including cyclohexanone, 2-cyclohexen-1-one, 2-hydroxycyclohexan-1-one, 1,2-cyclohexanedione, and 1,2,3,4,6,7,8,9-octahydrophenazine.

The term "main organic component" used herein means that this organic component constitutes the largest proportion in terms of quantity in gram COD/kg of a certain phase. The acronym "COD" stands for "Chemical Oxygen Demand" and is used herein to describe the quantity of organic components that can be oxidized in a given phase. Thus, the acronym "COD" is used herein to describe the oxidizable organic components content in a given phase.

The COD values are determined according to ASTM D 1252-95 (dichromate method).

In another embodiment of the invention, the aqueous ε-caprolactam phase of step d) comprises 50 to 85 wt. %, preferable 55 to 80 wt. % and more preferably 65 to 76 wt. % ε-caprolactam.

In a further embodiment of the invention, the aqueous ε-caprolactam phase of step d) comprises ammonium sulfate. In still further embodiment of the invention, the aqueous ε-caprolactam phase of step d) comprises 0.1 to 3 wt. %, preferable 0.15 to 1.5 wt. % and more preferably 0.3 to 1.0 wt. % ammonium sulfate.

In another embodiment of the invention, the aqueous ε-caprolactam phase of step d) comprises organic components as impurities (not including ε-caprolactam) in the amount of 1 to 40, preferably 2 to 25 and more preferably 4 to 15 gram COD/kg of the aqueous ε-caprolactam phase.

Step e)

In step e) of the process of the invention, the first aqueous ammonium sulfate phase obtained in step d) is treated. Step e) comprises several sub-steps.

In step e.1) of the process of the invention, the extraction of the first aqueous ammonium sulfate phase with a first organic solvent in the first extraction section is performed. The extraction results in a phase comprising first organic solvent and ε-caprolactam and in an extracted first aqueous ammonium sulfate phase. This extraction step has the advantage that ε-caprolactam is largely removed from the first aqueous ammonium sulfate phase. The extracted ε-caprolactam can be fed into concentration and purification processes for the production of first grade ε-caprolactam. At the same time, the extracted first aqueous ammonium sulfate phase has largely lost ε-caprolactam as impurity. In an embodiment of the invention, the extracted first aqueous ammonium sulfate phase is substantially free of ε-caprolactam. "Substantially free of ε-caprolactam" means that the extracted first aqueous ammonium sulfate phase comprises 0.005 to 0.3 wt. %, preferable 0.01 to 0.1 wt. % and more preferably 0.02 to 0.05 wt. % ε-caprolactam.

In an embodiment of the invention, the first organic solvent is an aromatic hydrocarbon, a halogenated hydrocarbon, a $C_4$-$C_{10}$ aliphatic alcohol and/or a cycloaliphatic alcohol. In a further embodiment of the invention, the first organic solvent is selected from the group consisting of benzene, toluene, chloroform, trichloroethane, 4-methyl-2-pentanol, 1-octanol, 2-ethylhexanol and mixtures thereof. Alternatively, the first organic solvent is selected from the group consisting of benzene, toluene, trichloroethylene, alcohols, and mixtures thereof. In a still further embodiment, benzene and toluene are preferred first organic solvents. All of these definitions and preferred subgroups also independently apply to the second organic solvent described further below.

In step e.2) of the process of the invention, the extracted first aqueous ammonium sulfate phase is charged to the first solvent recovery section, wherein first organic solvent and an aqueous ammonium sulfate phase are recovered. The recovered aqueous ammonium sulfate phase still contains organic components as impurities, but the first organic solvent is largely removed. This recovery step has the advantage that the first organic solvent can be reused in step e.1). In an embodiment of the invention, the organic components content of the aqueous ammonium sulfate phase of step e.2) is lower than the organic components content of the first aqueous ammonium sulfate phase of step d) wherein the organic components content is described in COD.

In step e.3) of the process of the invention, the recovered first aqueous ammonium sulfate phase is charged to the first evaporative type crystallization section wherein evaporative type crystallization is performed.

Examples of crystallizers which can be employed in a crystallization section are described in "Perry's Chemical Engineers Handbook" by Don W. Green and James O. Maloney, 7th edition, McGraw Hill, 1997, Section 18, pages 44-55. A crystallizer is usually operated at a temperature between 20 and 180° C. and at a pressure of between 2 kPa and 0.8 MPa.

Ammonium sulfate crystallization by evaporation of an aqueous ammonium sulfate phase as used herein typically involves heat input to evaporate water and concentrate the remaining phase. In order to reduce steam consumption needed for evaporative type crystallization in the production of crystals from an aqueous phase, a series of crystallizers can be integrated with respect to heat input (see, e.g., I. Kristjansson, Geothermics, 21 (1992); pp. 765-771). This is also preferred according to the invention. In a series of heat integrated crystallizers, water is boiled in a sequence of crystallizers, each held at a lower pressure than the previous one. Because the boiling temperature of water decreases as pressure decreases, the vapor boiled off in one crystallizer can be used to heat the next. Only the first crystallizer (operating at the highest pressure) requires an external source of heat. This is commonly done by passing steam at a high temperature into the reboiler of the first crystallizer in a series. The resulting lower temperature steam is used to heat the next crystallizer, and so on. This means that a series of crystallizers operates at descending temperatures. This type of crystallization is also called multiple-effect crystallization.

The recovered first ammonium sulfate phase fed to the first evaporative crystallizer in step e.3) comprises between 25 and 50 wt. %, preferably between 35 and 48 wt. %, and more preferably between 39 and 45 wt. % ammonium sulfate.

The organic components content of the recovered first ammonium sulfate phase fed to the first evaporative crystallizer in step e.3) is between 0.02 and 20 gram COD/kg, preferably between 0.05 and 15 gram COD/kg, and more preferably between 0.1 and 10 gram COD/kg of the recovered first ammonium sulfate phase.

In the first evaporative type crystallization section, crystalline ammonium sulfate and mother liquor are obtained by the evaporative type crystallization. The mother liquor is an aqueous ammonium sulfate phase enriched in organic components compared to the recovered first aqueous ammonium sulfate phase entering the first evaporative type crystallization section. Usually, the mother liquor is also enriched in ammonium sulfate.

In step e.4) of the process of the invention, mother liquor is discharged from the first evaporative type crystallization section. The discharge of a fraction of mother liquor is also called a purge. The purge in step e.4) has the advantage that it reduces the organic components content of the mother liquor remaining in the first evaporative type crystallization section. Keeping the organic components content low in the mother liquor remaining in the first evaporative type crystallization section improves the quality of the formed ammonium sulfate crystals, i.e., the ammonium sulfate crystals are less colored, contain fewer organic components, and the production of large crystals is facilitated. A lower limit for the organic components content in the mother liquor of the first evaporative type crystallization section is not critical, and is mainly determined by process economics since a larger fraction of mother liquor would need to be purged. Mother liquor may be withdrawn from the crystallizer by any means known to the skilled person. For example, clear liquor may be purged from the crystallizer's clarification zone, mother liquor that is removed as hydrocyclone overflow can be purged and/or mother liquor can be removed via a take out of a mother liquor circulation line. If the first evaporative type crystallization section operates as a multiple effect crystallization, the mother liquor can be discharged from any stage of the multiple effect crystallization. Preferably, it is discharged from the last stage of a multiple effect crystallization.

In an embodiment of the invention, the flow rate of the mother liquor which is purged from the first evaporative type crystallization section is between 0.5 and 30 parts by volume per unit of time, preferably between 1 and 25 parts by volume per unit of time, more preferably between 2 and 20 parts by volume per unit of time whereby the flow rate of the recovered first aqueous ammonium sulfate phase fed to the first evaporative crystallization section is 100 parts by volume per unit of time. If the flow rate of the mother liquor withdrawn from the first evaporative type crystallizer decreases, the organic components content in the mother liquor generally increases, presumed that the other flow settings remain unchanged, in particular the flow rate of the recovered first aqueous ammonium sulfate phase fed to the first evaporative crystallization section. If the feeding of the recovered first aqueous ammonium sulfate phase to the first evaporative type crystallizer and/or the purge of the mother liquor from the first evaporative type crystallizer occur(s) discontinuously or batch wise, it is to be understood that the before-mentioned flow rates are the average amounts fed or withdrawn per unit of time.

The mother liquor discharged from the first evaporative crystallizer in step e.4) usually comprises between 35 and 60 wt. %, preferably between 38 and 55 wt. % and more preferably between 42 and 52 wt. % ammonium sulfate.

The organic components content of the mother liquor discharged from the first evaporative type crystallization section usually is between 5 and 150 gram COD/kg, preferably between 10 and 75 gram COD/kg, and more preferably between 15 and 50 gram COD/kg of the mother liquor.

In step e.5) of the process of the invention, a slurry comprising crystalline ammonium sulfate is discharged from the first evaporative type crystallization section and charged to the first liquid-solid separation section to recover crystalline ammonium sulfate.

The term "slurry" used herein refers to an aqueous phase comprising solid matter. An ammonium sulfate slurry comprises ammonium sulfate crystals, dissolved ammonium sulfate, water and impurities. Typically, the impurities present in an ammonium sulfate slurry are organic components. Additionally, inorganic components can be present.

In an embodiment of the invention, step e.5) comprises the steps of

- e.5.1) discharging from the first evaporative type crystallization section a slurry comprising crystalline ammonium sulfate and charging said slurry to the first liquid-solid separation section;
- e.5.2) discharging crystalline ammonium sulfate from the first liquid-solid separation section and charging the crystalline ammonium sulfate to a first drying section, wherein dried crystalline ammonium sulfate is obtained.

The ammonium sulfate crystals obtained in step e.5) comprise besides ammonium sulfate itself, water and impurities. Typically, the impurities in ammonium sulfate crystals are organic components. Additionally, inorganic components can be present. Such inorganic components can be calcium and iron salts and silicon containing compounds.

Ammonium sulfate crystals of a larger size are preferred because they generally have a larger economic value. In an embodiment of the invention, the ammonium sulfate crystals produced in step e.5) have a mean median diameter greater than 0.8 mm. Preferably, the mean median diameter of the ammonium sulfate crystals produced in step e.5) is from 1.0 mm to 4.0 mm.

It is desirable to produce high purity grades of (almost) white colored crystalline ammonium sulfate for different applications. High purity ammonium sulfate crystals that are (almost) white colored are economically more valuable than brownish colored ammonium sulfate crystals with higher impurity levels. Typically, the color of high grade crystalline ammonium sulfate is white, off-white or light yellow. The ammonium sulfate crystals produced in step e.5) of the process of the invention are high grade crystals due to the sequence of processing steps e.1) to e.5). In an embodiment of the invention, the color of the ammonium sulfate crystals produced in step e.5) is white to off-white.

Formation of colored ammonium sulfate crystals comprising impurities in form of organic components is more pronounced during evaporative type crystallization at higher temperatures. Accordingly, it is advantageous to crystallize ammonium sulfate phases that contain organic components not at higher temperatures. This limits the temperature range at which the evaporative type crystallization can be performed. In order to avoid crystallizers that are operated at high temperatures, the number of crystallizers that can be operated in series becomes limited. The temperature at which a given ammonium sulfate phase may be crystallized without formation of colored crystals and without visible solid organic components is dependent on both the quantity and the composition of the organic components contained in the given ammonium sulfate phase. As a consequence, where two or more ammonium sulfate phases with different compositions of organic components are to be crystallized, different upper temperatures in the crystallizers may be used for each phase. Preferably, evaporative type crystallizers that crystallize ammonium sulfate from ammonium sulfate phases containing organic components are operated at a temperature below 120° C. More preferably, the evaporative type crystallizers are operated at a temperature below 110° C.

Step f)

In step f) of the process of the invention, the aqueous ε-caprolactam phase obtained in step d) is treated. Step f) comprises one or more sub-steps.

In step f.1) of the process of the invention, the aqueous ε-caprolactam phase is extracted in the second extraction section with a second organic solvent, whereby a phase comprising second organic solvent and ε-caprolactam, and a second aqueous ammonium sulfate phase comprising organic components are obtained. This aqueous ammonium sulfate phase is called "the second aqueous ammonium sulfate phase" throughout this disclosure to distinguish it from the first aqueous ammonium sulfate phase obtained directly from the neutralized Beckmann rearrangement mixture in step d).

In an embodiment of the invention, the second aqueous ammonium sulfate phase comprises between 0.1 and 10 wt. %, preferably between 0.2 and 8 wt. %, and more preferably between 0.5 and 6 wt. % ammonium sulfate.

In a further embodiment of the invention, the second aqueous ammonium sulfate phase of step f.1) has an organic components content between 5 and 200 gram COD/kg, preferably between 15 and 150 gram COD/kg, and more preferably between 20 and 100 gram COD/kg of the second aqueous ammonium sulfate phase.

In another embodiment of the invention, the second aqueous ammonium sulfate phase of step f.1) comprises as organic components cyclohexanone oxime, side-products of the Beckmann rearrangement reaction including cyclohexanone, 2-cyclohexen-1-one, 2-hydroxycyclohexan-1-one, 1,2-cyclohexanedione, and 1,2,3,4,6,7,8,9-octahydrophenazine, and second organic solvent.

The first aqueous ammonium sulfate phase of step d) and the second aqueous ammonium sulfate phase of step f.1) have in common that they comprise ammonium sulfate, water and organic components as impurities. The first and second aqueous ammonium sulfate phases can additionally contain inorganic components as impurities. Typically, the first and second aqueous ammonium sulfate phases differ from each other in at least the concentration of the contained organic components and ammonium sulfate. In one embodiment of the invention, the second aqueous ammonium sulfate phase of step f.1) has a higher organic components content than the recovered first aqueous ammonium sulfate phase obtained in step e2), whereby the organic components content is expressed in COD. In a different or further embodiment of the invention, the second aqueous ammonium phase of step f.1) has a lower ammonium sulfate content than the first aqueous ammonium sulfate phase of step d), whereby the ammonium sulfate content is expressed in wt. %.

The extraction of the aqueous ε-caprolactam phase of step d) is performed with a second organic solvent. The second organic solvent can, independent of the first organic solvent, be selected from the same list of solvents as defined for the first organic solvent above. For practical purposes, it is particularly advantageous if the same organic solvent is used as the first and second organic solvent.

In another embodiment of the invention, the second organic solvent is recovered from the second aqueous ammonium sulfate phase comprising organic components obtained in step f.1) prior to charging the resulting second aqueous phase comprising organic components to the second evaporative type crystallization section. This additional step, which will be referred to as f.2) has the advantage that the second organic solvent is recycled from the second aqueous ammonium sulfate phase and can thus be reused in step f.1). Another advantage of recovering the second organic solvent from the second aqueous ammonium sulfate phase is that said aqueous ammonium sulfate phase comprises less second organic solvent as impurity.

The phase comprising second organic solvent and ε-caprolactam which is obtained in the second extraction section in step f.1) apart from the second aqueous ammonium sulfate phase is further processed. Several concentration and purification processes for the production of first grade ε-caprolactam starting from the phase comprising second organic solvent and ε-caprolactam of step f.1) are known to the skilled person. Ullmann's Encyclopedia of Industrial Chemistry (2018) Chapter 'Caprolactam'; (https://doi.org/10.1002/14356007.a05_031.pub3) describes several (commercial) processes for the production of such first grade ε-caprolactam. Moreover, WO 02/070475 describes a process for recovering and purifying ε-caprolactam from an organic solvent. It discloses a procedure comprising the following steps, which is also envisioned as possible work-up for the ε-caprolactam comprising phase of the invention: a) washing the solution with water or an aqueous alkaline solution, resulting in a washed solution comprising ε-caprolactam and organic solvent and in a washing residue, b) evaporating organic solvent from the washed solution, resulting in ε-caprolactam product, c) optionally, hydrogenating the ε-caprolactam product, d) optionally, evaporating water from the ε-caprolactam product, e) distilling the ε-caprolactam product to recover ε-caprolactam and a distillation residue, f) extracting the distillation residue with an organic solvent in the presence of water to obtain (i) an extract comprising ε-caprolactam dissolved in organic solvent and (ii) an aqueous effluent, and g) recycling the extract to step a) or b).

The Second Evaporative Type Crystallization

In the process of the invention, a second evaporative type crystallization is performed in the so-called second evaporative type crystallization section. To the second type crystallization section (i) the mother liquor that is discharged from the first evaporative type crystallization section in step e.4) and/or (ii) the second aqueous ammonium sulfate phase comprising organic components that is obtained in step f.1) are/is charged.

In an embodiment of the invention, water is removed from the (ii) second aqueous ammonium sulfate phase comprising organic components obtained in step f.1) prior to charging the resulting concentrated second aqueous ammonium sulfate phase to the second evaporative type crystallization section.

The second evaporative type crystallization in the second type crystallization section is performed so that the following three-phase system occurs:

(1) a liquid oily phase comprising organic components;
(2) a crystalline ammonium sulfate phase; and
(3) a liquid aqueous ammonium sulfate comprising phase The term "performed so that" means that the second evaporative type crystallization section is operated under conditions which allow the generation of a three-phase system. In particular so much water is evaporated in the second evaporative type crystallization section from the aqueous feed(s) that the aqueous ammonium sulfate phase becomes oversaturated regarding both ammonium sulfate and organic components and as a result a liquid oily phase comprising organic components (1) and a crystalline ammonium sulfate phase (2) are formed next to a liquid aqueous ammonium sulfate comprising phase (3). Particular operation conditions of the second evaporative type crystallization section include that the organic components content and the weight fraction of ammonium sulfate of the liquid aqueous ammonium sulfate comprising phase in the second evaporative type crystallization section are at least 100 gram COD/kg of the liquid aqueous ammonium sulfate comprising phase mother liquor of which at least 5 gram COD/kg of the liquid aqueous ammonium sulfate comprising phase is originating from ε-caprolactam, and at least 36 wt. % ammonium sulfate, respectively.

The main difference between the first evaporative type crystallization performed in step e.3) and the second evaporative type crystallization is that the second evaporative type crystallization does not have a drain of mother liquor. Due to evaporation of water in the second evaporative type crystallization a more concentrated mother liquor is obtained in which the organic impurities are no longer soluble, leading not only to ammonium sulfate crystallization but also the generation of a liquid oily phase comprising the organic impurities. Thus, the main difference between the first and second evaporative crystallization section is the concentration of organic impurities: in the first evaporative crystallization section there is a supersaturation regarding ammonium sulfate and ammonium sulfate crystals are formed as a separate phase, however the mother liquor remains under-saturated regarding organic components (by purging a fraction of the mother liquor that contains impurities) and no separate oily liquid phase is formed.

Next to the evaporation conditions, also the feed streams to the first and second evaporative type crystallization section differ from each other. In an embodiment of the invention, the ammonium sulfate feeds (i) and/or (ii) to the second evaporative type crystallizer comprise(s) a higher organic components content than the recovered first aqueous ammonium sulfate phase charged to the first evaporative type crystallization section in step e.3), wherein the organic components content is expressed as COD. In a further embodiment, the ammonium sulfate content of the ammonium sulfate feeds (i) and/or (ii) to the second evaporative type crystallizer are/is lower than ammonium sulfate content of the recovered first aqueous ammonium sulfate phase charged to the first evaporative type crystallization section in step e.3), wherein the ammonium sulfate content is expressed in wt. %. In particular, the ammonium sulfate content of the ammonium sulfate feed (ii) to the second evaporative type crystallizer is lower than ammonium sulfate content of the recovered first aqueous ammonium sulfate phase charged to the first evaporative type crystallization section in step e.3), wherein the ammonium sulfate content is expressed in wt. %.

The second evaporative type crystallization according to the invention produces in particular a liquid oily phase, which is in step (iii) at least recovered from the three-phase system.

The term "recovered" as used herein means that material is isolated in form of a product, saved from loss and/or put to another use.

In an embodiment of the invention the liquid oily phase comprises ε-caprolactam, organic components, ammonium sulfate and water. The liquid oily phase is formed by evaporating so much water during the second evaporative type crystallization that the organic components become oversaturated and are no longer soluble in the liquid aqueous ammonium sulfate comprising phase on the second evaporative type crystallization section.

At least the liquid oily phase is recovered from the three-phase system generated in the second evaporative type crystallization section. For this purpose, the plant suitable to carry out the process of the invention can comprise in addition a second liquid-liquid separation section and a second liquid-solid separation section, whereby the recovery of at least the liquid oily phase in step (iii) comprises the steps of

- (iii.1) discharging from the second evaporative type crystallization section a mixture comprising liquid oily phase and liquid aqueous ammonium sulfate comprising phase and charging the same to the second liquid-liquid separation section, where the two phases are separated;
- (iii.2) recovering the separated liquid oily phase and the separated liquid aqueous ammonium sulfate comprising phase from the second liquid-liquid separation section;
- (iii.3) discharging from the second evaporative type crystallization section a slurry comprising crystalline ammonium sulfate and charging the same to the second liquid-solid separation section from which crystalline ammonium sulfate and a liquid aqueous ammonium sulfate phase are separately recovered.

Thus, by the process of the invention ammonium sulfate crystals can be obtained from the first aqueous ammonium sulfate phase of step d) and from the second aqueous ammonium sulfate phase of step f.1).

In a further embodiment of the invention, the weight ratio of the liquid oily phase to the liquid aqueous ammonium sulfate comprising phase of the mixture comprising the liquid oily phase and the liquid aqueous ammonium sulfate comprising phase that is discharged from the second evaporative type crystallization section and charged to the second liquid-liquid separation section in step (iii.1) is less than 2:1, preferably less than 1:1. In another embodiment of the invention the weight ratio of the liquid oily phase to the liquid aqueous ammonium sulfate comprising phase of the mixture comprising the liquid oily phase and the liquid aqueous ammonium sulfate comprising phase that is discharged from the second evaporative type crystallization section and charged to the second liquid-liquid separation section in step (iii.1) is from 1:0.5 to 1:50, preferably from 1:1 to 1:40, more preferably from 1:2 to 1:30, and most preferably from 1:4 to 1:15. In practice, good results were obtained when said ration was about 1:10.

In another embodiment of the invention,

- the liquid aqueous ammonium sulfate comprising phase recovered from the second liquid-liquid separation section in step (iii.2) and/or
- the liquid aqueous ammonium sulfate phase recovered from the second liquid-solid separation section in step (iii.3)

is/are charged to the second evaporative type crystallization section. This has the advantage that the liquid aqueous ammonium sulfate comprising phase recovered from the second liquid-liquid and/or the liquid aqueous ammonium sulfate phase recovered from the second liquid-solid separation section are used to produce crystalline ammonium sulfate in the second evaporative type crystallization section. Under these circumstances, the amount of crystalline ammonium sulfate produced in the second evaporative type crystallization is maximized in the process of the invention.

In another embodiment of the invention, the crystalline ammonium sulfate that is discharged from the second liquid-solid separation section in step (iii.3) is washed with an aqueous solution. This is advantageous because impurities associated with the crystalline ammonium sulfate are removed.

The ammonium sulfate crystals obtained in the second evaporative type crystallization section are usually of poorer quality in terms of size and/or color properties and/or caking behavior than those obtained from the first evaporative type crystallization section. However, there are also uses for poorer quality ammonium sulfate crystals (e.g., as fertilizer for less demanding applications, for instance for manual spreading applications) or they can be discharged as waste. The main purpose of the second evaporative type crystallization section according to the invention is the generation of the liquid oily phase with the advantages outlined above. In a particularly useful embodiment of the invention, the crystalline ammonium sulfate that is obtained from the second evaporative type crystallization section in step (i) is subsequently charged to a dissolving section, where the crystalline ammonium sulfate is dissolved in water, whereby an aqueous ammonium sulfate comprising phase is obtained that is charged to the first evaporative type crystallization section. This has the advantage that more high-grade ammonium sulfate crystals are obtained in the process of the invention overall, because the fraction yielding potentially poorer quality ammonium sulfate crystals is processed to produce a liquid oily phase containing the majority of impurities and a crystalline ammonium sulfate phase that can be dissolved and recycled into the first evaporative type crystallization section.

In an embodiment of the invention, the liquid oily phase has a density (measured at a temperature of 25° C.) that ranges between 1100 and 1275 kg/m$^3$, preferably between 1125 and 1250 kg/m$^3$ and most preferably between 1150 land 1225 kg/m$^3$. This has the advantage that a rather concentrated liquid oily phase is obtained, i.e., an oily phase with a high organics content and with a low water and a low ammonium sulfate content, which can be burned easily.

In a further embodiment of the invention, the liquid oily phase comprises between 0.5 and 25 wt. %, preferably between 1 and 20 wt. %, and more preferably between 2 and 15 wt. % ε-caprolactam and has an organic components content from 500 to 2000 gram COD/kg, preferably from 750 to 2000 gram COD/kg and more preferably from 1000 to 2000 gram COD/kg of the liquid oily phase. The aforementioned ranges of ε-caprolactam and organic components in the liquid oily phase can be combined with each other in any way. In particular, the ranges of the same "preference level" are compatible.

In another embodiment, the liquid oily phase comprises 1 to 30 wt. %, preferably 2 to 25 wt. %, and more preferably 5 to 20 wt. % of ammonium sulfate.

The liquid oily phase obtained by the process of the invention can be put to another use. In an embodiment of the invention the liquid oily phase is used as fuel in an incineration device. In another embodiment the liquid oily phase is used as fuel in an incineration device wherein at least part of the heat produced in the incineration device is used for the evaporation of water.

Ammonium Sulfate Crystals

The present invention further concerns crystalline ammonium sulfate that is produced in an evaporative type ammonium sulfate crystallization section in the presence of a liquid oily phase and a liquid aqueous ammonium sulfate comprising phase as described above in connection with the second evaporative type crystallization section.

The ammonium sulfate crystals produced in an evaporative type ammonium sulfate crystallization section in the presence of a liquid oily phase and a liquid aqueous ammonium sulfate comprising phase preferably have a mean median diameter greater than 0.6 mm. More preferably, the mean median diameter of the ammonium sulfate crystals produced in an evaporative type ammonium sulfate crystallization section in the presence of a liquid oily phase and a liquid aqueous ammonium sulfate comprising phase is from 0.8 mm to 3.0 mm.

In another embodiment of the invention, the ammonium sulfate crystals produced in the presence of a liquid oily phase and a liquid aqueous ammonium sulfate comprising phase and separated by filtration and washed with water comprise an organic components content from 0.2 to 250 gram COD/kg, preferably from 1 to 50 gram COD/kg, most preferably from 3 to 15 gram COD/kg of crystalline ammonium sulfate.

In a further embodiment of the invention, the color of the ammonium sulfate crystals produced in an evaporative type ammonium sulfate crystallization section in the presence of a liquid oily phase and a liquid aqueous ammonium sulfate comprising phase is (light) brownish.

Liquid Oily Phase

The present invention further concerns a liquid oily phase comprising

- between 0.5 and 25 wt. %, preferably between 1 and 20 wt. %, and more preferably between 2 and 15 wt. % ε-caprolactam; and
- organic components in an amount of from 500 to 2000 gram COD/kg, preferably 750 to 2000 gram COD/kg and more preferably 1000 to 2000 gram COD/kg of the liquid oily phase.

With regard to the properties and use of the liquid oily phase, the same applies as has been already descripted in connection with the process of the invention.

The Plant

The present invention also concerns an ammonium sulfate crystallization plant for the production of crystalline ammonium sulfate from aqueous streams comprising organic components whereby the aqueous streams comprising organic components originate from an ε-caprolactam production process.

The plant of the present invention is an industrial scale plant that comprises at least a Beckmann rearrangement reaction section, a neutralization section, a first liquid-liquid separation section, a first and a second extraction section, a first solvent recovery section, a first and a second evaporative type crystallization section, and a first liquid-solid separation section, wherein the plant is configured for carrying out the process of the present invention.

The capacity of the ammonium sulfate crystallization plant is typically selected based on the volume of ammonium sulfate phases(s) discharged from plants for the production of ε-caprolactam.

The production capacity of ammonium sulfate crystals in the industrial scale ammonium sulfate plant of the invention is on the scale of several thousands of tons per year (kilotons per annum; kta). In an embodiment of the invention, the production capacity of ammonium sulfate crystals in the industrial scale plant is more than 10,000 tons per annum (10 kta). Preferably, the production capacity of ammonium sulfate crystals in the industrial scale plant is from 100 kta to 2,000 kta. More preferably, the production capacity of ammonium sulfate crystals in the industrial scale plant is from 150 kta to 1,500 kta.

BRIEF DESCRIPTION OF THE DRAWINGS

In the following, the invention will be described with reference to the Figures, which depict certain embodiments of the invention. The invention, however, is as defined in the claims and as generally described herein. It should not be limited to the embodiments shown for illustrative purposes in the Figures below.

FIG. 1 describes the three alternative modes of the process of the invention.

DESCRIPTION OF THE DRAWINGS

FIG. 1 indicates the alternative modes of the process of the invention.

Figure 1A:
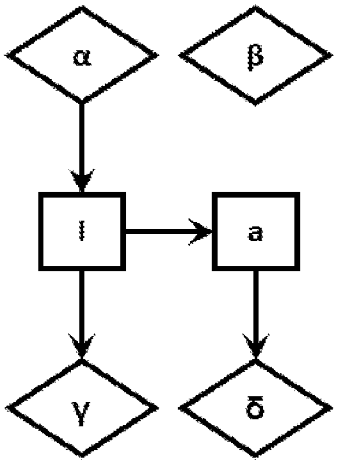
FIG. 1A describes an alternative mode of the process of the invention in which a second evaporative type crystallization section is fed only with mother liquor produced in a first evaporative type crystallization section.

In FIG. 1A, a first aqueous ammonium sulfate phase [α] obtained from a neutralized Beckmann rearrangement mixture is processed and used for evaporative type crystallization in a first evaporative type crystallization section [I]. During evaporative type crystallization crystalline ammonium sulfate [γ] and mother liquor is obtained. The crystalline ammonium sulfate [γ] is recovered. The mother liquor is an aqueous ammonium sulfate phase enriched in organic components compared to the processed first aqueous ammonium sulfate phase entering the first evaporative type crystallization section [I]. A fraction of the mother liquor is discharged from the first evaporative type crystallization section [I] to the second evaporative type crystallization section [a]. A second aqueous ammonium sulfate phase [β] generated by extracting an aqueous ε-caprolactam phase obtained from a neutralized Beckmann rearrangement mixture is not charged to the second evaporative type crystallization section [a]. In the second evaporative type crystallization section evaporative crystallization is performed so that a three-phase system arises. Said three-phase system comprises a liquid oily phase, a crystalline ammonium sulfate phase and a liquid aqueous ammonium sulfate comprising phase. At least the liquid oily phase [δ] is recovered.

Figure 1B:
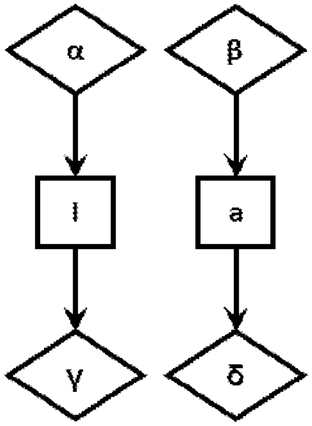
FIG. 1B describes an alternative mode of the process of the invention in which a second evaporative type crystallization section is fed only with a second aqueous ammonium sulfate phase generated by extracting an aqueous ε-caprolactam phase of a neutralized Beckmann rearrangement mixture.

In FIG. 1B, a first aqueous ammonium sulfate phase [α] obtained from a neutralized Beckmann rearrangement mixture is processed and used for evaporative type crystallization in a first evaporative type crystallization section [I]. During evaporative type crystallization crystalline ammonium sulfate [γ] and mother liquor is obtained. Optionally, a fraction of the mother liquor is discharged from the first evaporative type crystallization section [I] to outside the process (not shown). The crystalline ammonium sulfate [γ] is recovered. A second aqueous ammonium sulfate phase [β] generated by extracting an aqueous ε-caprolactam phase obtained from a neutralized Beckmann rearrangement mixture is charged to a second evaporative type crystallization section [a]. In the second evaporative type crystallization section evaporative crystallization is performed so that a three-phase system arises. Said three-phase system comprises a liquid oily phase, a crystalline ammonium sulfate phase and a liquid aqueous ammonium sulfate comprising phase. At least the liquid oily phase [δ] is recovered.

Figure 1C:
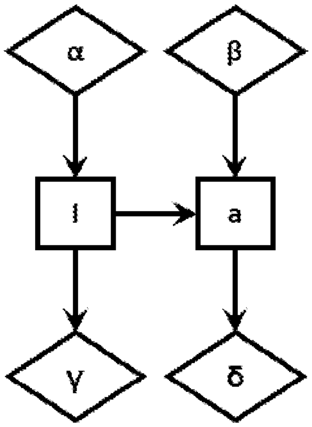
FIG. 1C describes an alternative mode of the process of the invention in which a second evaporative type crystallization section is fed with both mother liquor produced in a first evaporative type crystallization section and a second aqueous ammonium sulfate phase generated by extracting an aqueous ε-caprolactam phase of a neutralized Beckmann rearrangement mixture.

FIG. 1C combines the alternative modes of the process of the invention described in FIG. 1A and FIG. 1B. In FIG. 1C a fraction of the mother liquor in the first evaporative type crystallization section [I] is charged to the second evaporative type crystallization section [a]. In addition, the second aqueous ammonium sulfate phase [β] is charged to a second evaporative type crystallization section [a].

Figure 2:
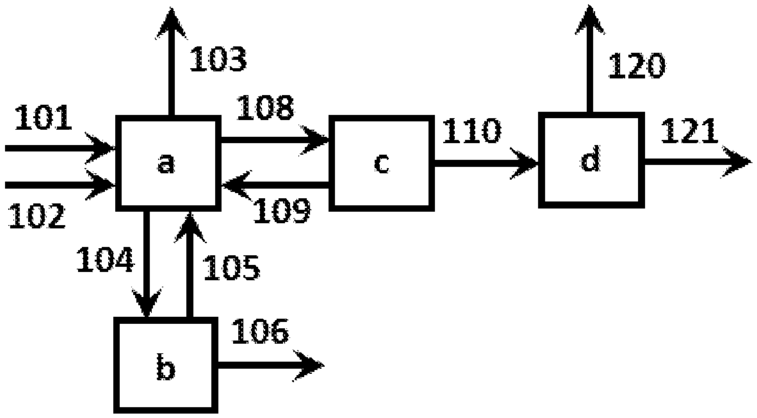
FIG. 2 describes an embodiment of the present invention, wherein two feeds comprising ammonium sulfate and organic components are fed to a second evaporative type crystallization section: On the one hand, mother liquor produced in a first evaporative type crystallization section is charged to the second evaporative type crystallization section. On the other hand, a second aqueous ammonium sulfate phase generated by extracting an aqueous ε-caprolactam phase of a neutralized Beckmann rearrangement mixture is charged to the second evaporative type crystallization section. In the second evaporative type crystallization section evaporative type crystallization is performed so that a three-phase system arises comprising a liquid oily phase, a crystalline ammonium sulfate phase and a liquid aqueous ammonium sulfate comprising phase. The liquid oily phase and the crystalline ammonium sulfate are recovered in the process.

In FIG. 2, the following two different ammonium sulfate comprising feeds [101] and [102] are charged to one or more evaporative type crystallizers in evaporative crystallization section [a] (e.g., Oslo (fluidized bed) crystallizers, draft tube baffle (DTB) crystallizers, forced circulation crystallizers): Mother liquor enriched in organic components [101], which was purged from an ammonium sulfate crystallization section, and a second aqueous ammonium sulfate phase comprising organic components, which was obtained as effluent from an extraction of a crude aqueous ε-caprolactam phase with an organic solvent. Optionally, prior to being charged to one or more evaporative type crystallizers in evaporative crystallization section [a], the second aqueous ammonium sulfate phase [102] comprising organic components is charged to a solvent recovery section, in which solvent is recovered (not shown). Optionally, prior to being charged to one or more evaporative type crystallizers in evaporative crystallization section [a], the second aqueous ammonium sulfate phase [102] comprising organic components is charged to a pre-concentration section, in which mainly water is removed, e.g., via evaporation and/or membrane filtration (not shown).

The water evaporated in the one or more evaporative type crystallizers in evaporative crystallization section [a] is condensed and discharged as condensate [103]. Generally, the condensate [103] is disposed of as waste and is treated in a waste water treatment system (not shown). Optionally, condensate [103] is re-used, optionally after purification treatment (e.g., adsorption treatment by activated carbon), for the Beckmann rearrangement reaction (not shown).

The concentration of organic components and the concentration of ammonium sulfate in the one or more evaporative type crystallizers in evaporative crystallization section [a] are so high that a three-phase system occurs: a liquid oily phase with a high organic components content, a liquid aqueous ammonium sulfate comprising phase and a crystalline ammonium sulfate phase.

A mixture [104] comprising liquid oily phase and liquid aqueous ammonium sulfate comprising phase is discharged from the one or more evaporative type crystallizers in evaporative crystallization section [a] and charged to a liquid-liquid separation section [b]. This mixture might also contain small amounts of the crystalline ammonium sulfate phase. A liquid-liquid separation section [b] consists of one or more separation vessels, in which, for example, a liquid oily phase with a high organic components content separates off as top layer and a liquid aqueous ammonium sulfate comprising phase (and optionally a crystalline ammonium sulfate phase) as bottom layer.

The liquid oily phase [106] is recovered from the liquid-liquid separation section [b]. Optionally, this liquid oily phase [106] is charged to an incinerator (not shown). It can also be stored and/or used or sold as fuel. Optionally, part of the heat that is produced by burning the liquid oily phase in the incinerator is used to generate steam (not shown).

A liquid aqueous ammonium sulfate phase [105] (and optionally an ammonium sulfate crystals comprising solid phase), is/(are) also discharged from the liquid-liquid separation section [b] and charged to the one or more evaporative type crystallizers in evaporative crystallization section [a].

An ammonium sulfate containing slurry [108] comprising liquid aqueous ammonium sulfate comprising phase and ammonium sulfate crystals is discharged from the one or more evaporative type crystallizers of evaporative type crystallization section [a] and charged to one or more liquid-solid separation devices in liquid-solid separation section [c] (e.g., (continuous) filters, centrifuges, decanters, elutriation columns, salt legs, hydrocyclones or combination thereof). In the liquid-solid separation section [c] wet ammonium sulfate crystals [110] are separated off from the liquid aqueous ammonium sulfate comprising phase. Optionally, this is followed by a washing step of the wet ammonium sulfate crystals, whereby the wet ammonium sulfate crystals are washed (preferably with water or an aqueous ammonium sulfate phase) in order to reduce the organic components content (adhering to the surface) of the wet ammonium sulfate crystals (not shown). The remainder, an aqueous ammonium sulfate phase or a diluted ammonium sulfate slurry [109] is charged back to the one or more evaporative type crystallizers [a].

The wet ammonium sulfate crystals [110] are dried in one or more drying devices in drying section [d] (e.g., fluidized bed dryers), whereby water vapor [120] and dried ammonium sulfate crystals [121] are obtained and separately discharged. Optionally, the dried ammonium sulfate crystals [121] are sieved, coated and/or blended with other compounds (not shown).

Figure 3:
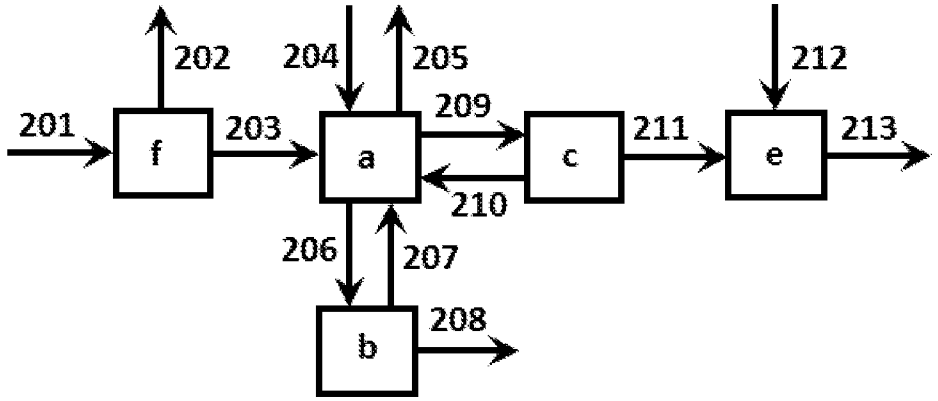
FIG. 3 describes another embodiment of the present invention, wherein two feeds comprising ammonium sulfate and organic components are fed to a second evaporative type crystallization section: On the one hand, mother liquor produced in a first evaporative type crystallization section is charged to the second evaporative type crystallization section. On the other hand, a second aqueous ammonium sulfate phase generated by extracting an aqueous ε-caprolactam phase of a neutralized Beckmann rearrangement mixture is charged to the second evaporative type crystallization section. Prior to charging the second aqueous ammonium sulfate phase to the second evaporative type crystallization section said phase is concentrated in a pre-concentration section. In the second evaporative type crystallization section evaporative type crystallization is performed so that a three-phase system arises comprising a liquid oily phase, a crystalline ammonium sulfate phase and a liquid aqueous ammonium sulfate comprising phase. All three phases are further treated. The crystalline ammonium sulfate is dissolved in a dissolution section. The liquid oily phase is recovered in the process.

In FIG. 3, an aqueous ammonium sulfate phase [201] comprising organic components which was obtained as effluent by extracting a crude aqueous ε-caprolactam phase with an organic solvent is charged to pre-concentration section [f], in which mainly water is removed. Preferably, the pre-concentration section [f] comprises reverse osmosis membranes and/or one or more evaporators, e.g., falling film type, natural circulation type, forced circulation type, rising film type, climbing-film plate type, or combinations thereof. Optionally, prior to being charged to a pre-concentration section [f], the aqueous ammonium sulfate phase [201] comprising organic components is charged to a solvent recovery section, in which solvent is recovered (not shown). Water is separated off in the pre-concentration section [f] and is discharged as water flow [202]. Generally, the water flow [202] is disposed of as waste and is treated in a waste water treatment system (not shown). Optionally, water flow [202] is re-used, optionally after purification treatment (e.g., adsorption treatment by activated carbon), for the Beckmann rearrangement reaction (not shown). Optionally, in case water flow [202] is in the vapor phase (e.g., as a result of evaporation) then the heat of condensation might be recovered (not shown).

Pre-concentrated effluent [203] is discharged from the pre-concentration section [f] and is charged to one or more evaporative type crystallizers in an ammonium sulfate crystallization section [a] (e.g., Oslo (fluidized bed) crystallizers, draft tube baffle (DTB) crystallizers, forced circulation crystallizers). Optionally, for pH-adjustment, (aqueous) ammonia is charged to pre-concentrated effluent [203] prior to the charging to one or more evaporative type crystallizers in the ammonium sulfate crystallization section [a] (not shown). In addition, an aqueous ammonium sulfate phase comprising organic components which was purged from another ammonium sulfate crystallization section [204] is charged to one or more evaporative type crystallizers in the ammonium sulfate crystallization section [a].

Water which is evaporated in the one or more evaporative type crystallizers in the ammonium sulfate crystallization section [a] is condensed and discharged as condensate [205]. Generally, the condensate [205] is disposed of as waste and is treated in a waste water treatment system (not shown). Optionally, condensate [205] is re-used, optionally after purification treatment (e.g., adsorption treatment by activated carbon), in the process for the production of ammonium sulfate and ε-caprolactam based on cyclohexanone oxime that is produced from cyclohexanone (not shown).

The concentration of organic components and the concentration of ammonium sulfate in the one or more evaporative type crystallizers in ammonium sulfate crystallization section [a] are so high that a three-phase system occurs: a liquid oily phase with a high organic components content, a liquid aqueous ammonium sulfate comprising phase and a crystalline ammonium sulfate phase.

A mixture comprising mainly liquid oily phase with a high organic components content and liquid aqueous ammonium sulfate comprising phase [206] is discharged from the one or more evaporative type crystallizers in ammonium sulfate crystallization section [a] and charged to a liquid-liquid separation section [b]. This mixture might also contain small amounts of crystalline ammonium sulfate phase. A liquid-liquid separation section [b] consists of one or more separation vessels, in which liquid oily phase with a high organic components content separates off as top layer and liquid aqueous ammonium sulfate comprising phase as bottom layer. Optionally, the bottom layer also contains a low fraction (<4 wt. %) of crystalline ammonium sulfate phase.

The top layer is recovered from the liquid-liquid separation section [b] as liquid oily phase [208]. Optionally, this liquid oily phase [208] is charged to an incinerator (located on-site or optionally not on-site) (not shown). Optionally, part of the heat that is produced by burning the liquid oily phase in the incinerator is used to generate steam (not shown).

The bottom layer, a liquid aqueous ammonium sulfate comprising phase (that optionally contains crystalline ammonium sulfate phase), is discharged from the liquid-liquid separation section [b] as aqueous phase [207] and is charged to the one or more evaporative type crystallizers in ammonium sulfate crystallization section [a].

Ammonium sulfate containing slurry [209] is discharged from the one or more evaporative type crystallizers of the ammonium sulfate crystallization section [a] and is charged to one or more liquid-solid separation devices in liquid-solid separation section [c] (e.g., (continuous) filters, centrifuges, decanters, elutriation columns, salt legs, hydrocyclones or combination thereof). In the liquid-solid separation section [c] wet ammonium sulfate crystals [211] are separated off. Optionally, a washing step of the wet ammonium sulfate crystals is included, whereby the wet ammonium sulfate crystals are washed (preferably with water or an aqueous ammonium sulfate phase) in order to reduce the organic components content (adhering to the surface) of the wet ammonium sulfate crystals (not shown).

The remainder, a liquid aqueous ammonium sulfate comprising phase or a diluted ammonium sulfate slurry [210] is charged back to the one or more evaporative type crystallizers in ammonium sulfate crystallization section [a].

The wet ammonium sulfate crystals [211] and a water comprising phase [212] are charged to an ammonium sulfate dissolution section [e]. Preferably, the water comprising phase [212] comprises more than 90 wt. % water. Optionally, the water comprising phase [212] comprises ammonium sulfate. Generally, the ammonium sulfate dissolution section [e] consists of one or more vessels which contain a mixing compartment and an overflow compartment. An aqueous flow of ammonium sulfate [213] is discharged from the ammonium sulfate dissolution section [e]. Preferably, the aqueous flow of ammonium sulfate [213] is an aqueous phase that contains about 40 wt. % ammonium sulfate and does not contain any solid ammonium sulfate crystals. Preferably, the aqueous flow of ammonium sulfate [213] is charged as feed to an ammonium sulfate crystallization section, in which crystalline ammonium sulfate, aqueous condensate and a purge are produced.

Figure 4:
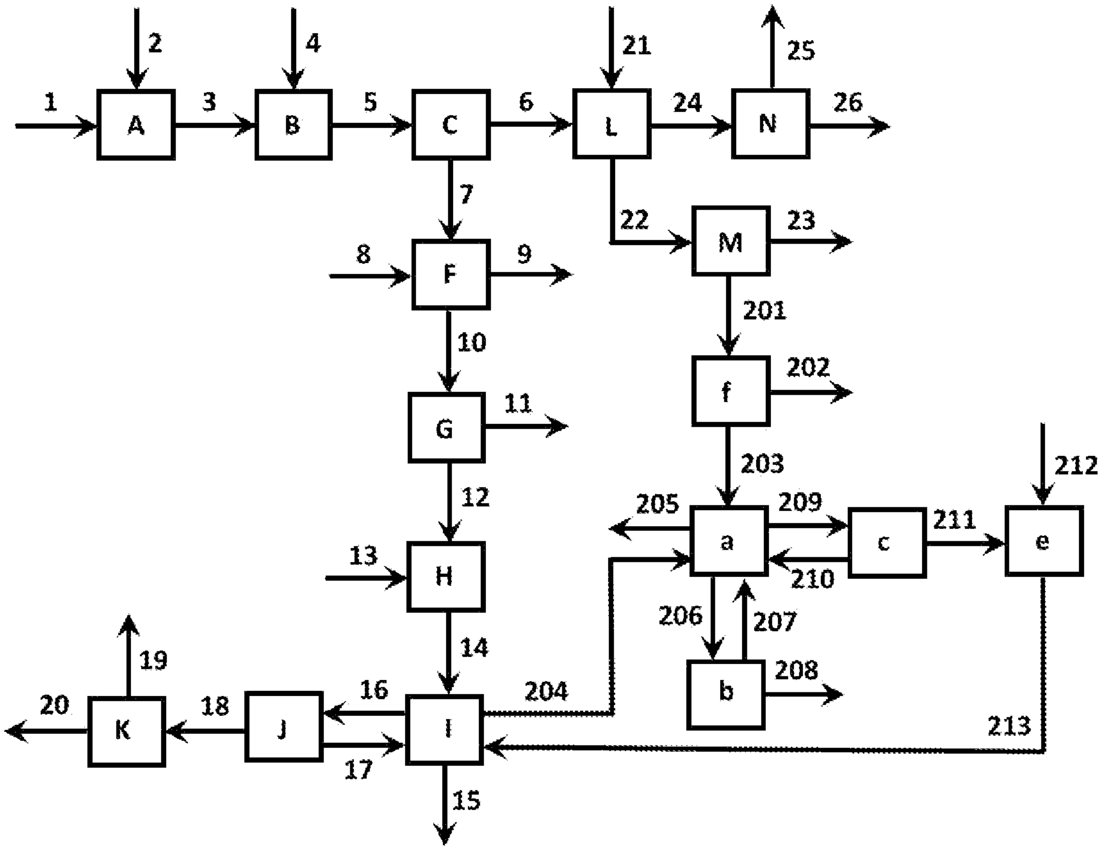
FIG. 4 describes an embodiment of the present invention, wherein a cyclohexanone oxime is subjected to a Beckmann rearrangement reaction in the presence of oleum so that ε-caprolactam is produced. The Beckmann rearrangement reaction mixture comprising ε-caprolactam is neutralized. The neutralized Beckmann rearrangement mixture comprises two phases, a first aqueous ammonium sulfate phase and an ε-caprolactam phase. Both phases of the neutralized Beckmann rearrangement mixture are further processed. In the further course of the process two aqueous ammonium sulfate phases comprising organic components are treated: On the one hand, a first aqueous ammonium sulfate phase directly obtained from the neutralized Beckmann rearrangement mixture is treated. On the other hand, a second aqueous ammonium sulfate phase is treated which is obtained by extracting an aqueous ε-caprolactam phase of a neutralized Beckmann rearrangement mixture.

In FIG. 4, cyclohexanone oxime [1] and oleum [2] are charged to a Beckmann rearrangement section [A]. The cyclohexanone oxime might be produced by various technologies. One option is the HPO® technology, in which cyclohexanone oxime is formed by reacting hydroxylamine obtained by hydrogenation of nitrate and cyclohexanone. Another option to produce cyclohexanone oxime is the ammoximation technology, in which cyclohexanone oxime is formed by reacting ammonia, hydrogen peroxide and cyclohexanone. A further option to produce cyclohexanone oxime is the Raschig technology in which cyclohexanone oxime is formed by reacting hydroxylamine obtained by the reduction of nitrite and cyclohexanone.

The Beckmann rearrangement mixture [3] and an aqueous ammonia phase [4] are added to a neutralization section [B] so that a neutralized Beckmann rearrangement mixture [5] is produced. Alternatively, the aqueous ammonia phase [4] is replaced by separate additions of water and gaseous ammonia (not shown). A neutralized mixture containing an aqueous ammonium sulfate phase and an aqueous crude ε-caprolactam phase are obtained in the neutralization section [B]. The aqueous ammonium sulfate phase comprises ε-caprolactam and organic components as impurities. The aqueous crude ε-caprolactam phase comprises ammonium sulfate and organic components as impurities.

The neutralized mixture [5] is charged to a liquid-liquid separation section [C], in which the aqueous ammonium sulfate phase and the aqueous crude ε-caprolactam phase are separated from each other by phase separation. The aqueous crude ε-caprolactam phase [6] and the aqueous ammonium sulfate phase [7] leave the liquid-liquid separation section [C].

The aqueous ammonium sulfate phase [7] is charged to an extraction section [F], in which a solvent [8] is added to recover dissolved ε-caprolactam. Various solvents can be used, e.g., benzene, toluene, trichloroethylene, and alcohols, inter alia 1-octanol and 2-ethylhexanol and mixtures of alcohols. Extraction section [F] might comprise one or more extraction units, e.g., (counter-current) extraction columns and mixer-settlers. A mixture comprising ε-caprolactam and solvent [9] leaves the extraction section [F].

The obtained extracted aqueous ammonium sulfate phase [10] is charged to a solvent recovery section [G], in which the solvent is recovered from the extracted aqueous ammonium sulfate phase [10] and is discharged as recovered solvent [11]. Solvent recovery section [G] might comprise one or more distillation columns and/or one or more steam strippers.

The aqueous ammonium sulfate phase after solvent recovery [12] is pH-adjusted by addition of pH modifying agent [13] (preferably ammonia or sulfuric acid) in a pH-adjustment section [H], whereby a pH-adjusted aqueous ammonium sulfate phase [14] is obtained.

The pH-adjusted aqueous ammonium sulfate phase [14] is charged to one or more evaporative type crystallizers in evaporative type crystallization section [I] (e.g., an Oslo (fluidized bed) crystallizer, a draft tube baffle (DTB) crystallizer or a forced circulation crystallizer). Vapor recompression and/or multiple-effect evaporation might be applied in order to reduce energy consumption required for the evaporation of water in the ammonium sulfate crystallizer(s). Aqueous flow of ammonium sulfate [213] that is discharged from the ammonium sulfate dissolution section [e] is charged to one or more evaporative type crystallizers in evaporative type crystallization section [I]. The water evaporated in the one or more evaporative type crystallizers in evaporative type crystallization section [I] is condensed and discharged as condensate [15]. Optionally, condensate [15] is re-used, optionally after purification treatment (e.g., adsorption treatment by activated carbon), for the Beckmann rearrangement reaction (not shown). A purge [204] is discharged from one or more evaporative type crystallizers in the evaporative type crystallization section [I]. Purge [204] is mother liquor which is an aqueous ammonium sulfate phase with an increased organic components content compared to the organic components content of the charged pH-adjusted aqueous ammonium sulfate phase [14]. Purge [204] is charged to the second evaporative type crystallization section [a].

An ammonium sulfate containing slurry [16] is discharged from the one or more evaporative type crystallizers in evaporative type crystallization section [I] and is charged to one or more liquid-solid separation devices [J] (e.g., (continuous) filters, centrifuges, decanters, elutriation columns, salt legs, hydrocyclones or combination thereof), whereby wet ammonium sulfate crystals [18] are separated off. The remainder, an aqueous ammonium sulfate phase or a diluted ammonium sulfate slurry [17] is charged to the one or more evaporative type crystallizers in evaporative type crystallization section [I].

Optionally, a washing step of the wet ammonium sulfate crystals is included, whereby the wet ammonium sulfate crystals are washed (preferably with water or an aqueous ammonium sulfate phase) in order to reduce the content of organic components (adhering to the surface) of the wet ammonium sulfate crystals (not shown).

The wet ammonium sulfate crystals [18] are dried in one or more drying devices [K] (e.g., fluidized bed dryers), whereby water vapor [19] and dried ammonium sulfate crystals [21] are discharged. Optionally, the dried ammonium sulfate crystals [20] are sieved, coated and/or blended with other compounds (not shown).

In extraction section [L], the aqueous crude ε-caprolactam [6] is extracted with a solvent [21], whereby an aqueous effluent [22] and a mixture comprising ε-caprolactam and solvent [25] are obtained. Various solvents can be used, e.g., benzene, toluene, trichloroethylene, and alcohols, inter alia 1-octanol and 2-ethylhexanol and mixtures thereof. Extraction section [L] might comprise one or more extraction units, e.g., (counter-current) extraction columns and mixer-settlers. The obtained aqueous effluent [22] is charged to a solvent recovery section [M].

In solvent recovery section [M] solvent is recovered from the aqueous effluent [22] and is discharged as recovered solvent [23]. Solvent recovery section [M] might comprise one or more distillation columns and/or one or more steam strippers. The resulting aqueous effluent after solvent recovery [201] is charged to a pre-concentration section [f], in which mainly water is removed. Preferably, the pre-concentration section [f] comprises reverse osmosis membranes and/or one or more evaporators, e.g., falling film type, natural circulation type, forced circulation type, rising film type, climbing-film plate type, or combinations thereof. Water is separated off in the pre-concentration section [f] and is discharged as water flow [202]. Generally, the water flow [202] is disposed of as waste and is treated in a waste water treatment system (not shown). Optionally, water flow [202] is re-used, optionally after purification treatment (e.g., adsorption treatment by activated carbon), for the Beckmann rearrangement reaction (not shown). Optionally, in case water flow [202] is in the vapor phase (e.g., as a result of evaporation) then the heat of condensation might be recovered (not shown).

The mixture comprising ε-caprolactam and solvent [24] that is discharged from extraction section [L] is further worked-up in an ε-caprolactam purification and concentration section [N], whereby recovered solvent [25] and purified ε-caprolactam [26] are obtained. In industrial practice, various embodiments of ε-caprolactam purification and concentration section [N] are realized. Generally, these embodiments might comprise of a combination of units for extraction, hydrogenation, ion exchange, crystallization, pH-adjustment and/or (vacuum) distillation.

Sections [a], [b], [c], and [e] in FIG. 4 and the various in- and outflows from these sections are as described for FIG. 3 above.

EXAMPLES

The following examples serve to explain the invention in more detail, in particular with regard to certain forms of the invention. The examples, however, are not intended to limit the present disclosure.

The COD contents mentioned in the following examples are determined in accordance with the dichromate method according to ASTM D 1252-95.

The Examples and the Comparative Examples were carried out in industrial-scale continuously operating plants with annual capacities above 200 kta ε-caprolactam, in which both ε-caprolactam and crystalline ammonium sulfate were produced.

Comparative Example 1

Comparative Example 1 is very similar to the embodiment of the invention depicted in FIG. 4. In the Comparative Example, however, the aqueous effluent after benzene recovery [201] was charged to a waste water treatment system. In addition, the purge [204] was charged to a waste water treatment system.

In a commercial caprolactam plant cyclohexanone oxime was produced according to the HPO® process from cyclohexanone. The cyclohexanone oxime [1] was converted into ε-caprolactam in a three-stage Beckmann rearrangement reaction section [A] with oleum [2]. The resulting Beckmann rearrangement mixture [3] (sulfate of ε-caprolactam in excess sulfuric acid) was then neutralized with aqueous ammonia [4] in a neutralization section [B], whereby a neutralized mixture of aqueous crude ε-caprolactam and an aqueous ammonium sulfate phase [5] were obtained. These two phases were separated in liquid-liquid separation section [C] into aqueous crude ε-caprolactam [6] and an aqueous ammonium sulfate phase [7].

The aqueous crude ε-caprolactam [6] was extracted with benzene [21] in a counter-current extraction column in extraction section [L], whereby a benzenic-ε-caprolactam mixture [24] and an aqueous effluent [22] were obtained. The benzenic-ε-caprolactam mixture [24] was further worked-up in ε-caprolactam purification and concentration section [N], whereby recovered benzene [25] and first grade ε-caprolactam [26] were obtained. The first grade ε-caprolactam [26] was sold as raw material for nylon-6 production. The aqueous effluent [22] was fed to a distillation column in benzene recovery section [M] from which benzene [23] was recovered as top product and an aqueous effluent after benzene recovery [201] was obtained as bottom product. The aqueous effluent after benzene recovery [201] consisted of ca. 4 wt. % ammonium sulfate, ca. 4 wt. % organic components and the remainder was mainly water. In Comparative Example 1, the aqueous effluent after benzene recovery [201] was charged to a waste water treatment system, in which most of the ammonium and organic components were removed.

The aqueous ammonium sulfate phase [7] was charged to the upper-part and benzene [8] was charged to the lower part of a counter-current extraction column in extraction section [F]. A benzenic-ε-caprolactam comprising mixture [9] and an extracted aqueous ammonium sulfate phase [10] were discharged from the extraction section [F]. The extracted aqueous ammonium sulfate phase [10] was fed to a distillation column in a benzene recovery section [G] from which benzene [11] was recovered as top product and an aqueous ammonium sulfate phase after benzene recovery [12] was obtained as bottom product. The aqueous ammonium sulfate phase after solvent recovery [12] was pH-adjusted to a pH value of about 5 (measured at a temperature of 25° C.) by addition of aqueous ammonia [13] in pH-adjustment section [H], whereby a pH-adjusted aqueous ammonium sulfate phase [14] was obtained.

This pH-adjusted aqueous ammonium sulfate phase [14] was charged to three Oslo type crystallizers with multi-effect evaporation in evaporative type crystallization section [I]. The water evaporated in evaporative type crystallization section [I] was condensed and discharged as condensate [15]. In Comparative Example 1, the purge [204] was discharged from evaporative type crystallization section [I]. The purge [204] was then charged to a waste water treatment system, in which most of the ammonium and organic components were removed. Purge [204] consisted of water, about 40 wt. % ammonium sulfate and organic impurities (about 40 gram COD/kg of the purge).

An ammonium sulfate containing slurry [16] was discharged from evaporative type crystallization section [I] and was charged to centrifuges in a liquid-solid separation section [J], in which, after washing with water, wet ammonium sulfate crystals [18] were separated off. The remainder, an ammonium sulfate phase with some fine ammonium sulfate crystals in it [17] was charged to the evaporative type crystallization section [I]. Finally, the wet ammonium sulfate crystals [18] were dried in a fluidized bed dryer in drying section [K], whereby water vapor [19] and dried ammonium sulfate crystals [20] were discharged. The dried ammonium sulfate crystals [20] were screened before being sold as high grade crystalline ammonium sulfate. The dried ammonium sulfate crystals [20] had a mean median diameter of almost 3 mm and the color was whitish.

Example 1

Example 1 describes an embodiment of the invention as depicted in FIG. 4.

The experiment described in Comparative Example 1 was repeated, with the difference that now the purge [204] and the aqueous effluent after benzene recovery [201] were not charged to a waste water treatment system, but were charged to an apparatus, that comprises a pre-concentration section [f], an ammonium sulfate crystallization section [a], a liquid-liquid separation section [b], a liquid-solid separation section [c], and an ammonium sulfate dissolution section [e]. From this apparatus an aqueous flow of ammonium sulfate phase [213] was charged to the first ammonium sulfate crystallization section [I]. From the liquid-liquid separation section [b] a liquid oily phase with a high content of organic components [208] was discharged and combusted in an incinerator.

The aqueous effluent after benzene recovery [201], that consisted of ca. 4 wt. % ammonium sulfate, ca. 4 wt. % organics and the remainder mainly being water, was charged to a steam-heated falling film evaporator in pre-concentration section [f], whereby a portion of the water was evaporated that was discharged as vapor [202].

The obtained pre-concentrated effluent [203] consisting of ca. 8 wt. % ammonium sulfate, ca. 8 wt. % organic components and the remainder mainly being water, was discharged from the falling film evaporator in pre-concentration section [f] and was charged to an Oslo crystallizer in ammonium sulfate crystallization section [a], preceded by charging aqueous ammonia for pH adjustment. In addition, purge [204] that was discharged from evaporative type crystallization section [I] was charged to the Oslo crystallizer in ammonium sulfate crystallization section [a]. Vapor [202] was fed to a heat exchanger of the Oslo crystallizer in ammonium sulfate crystallization section [a]. Water was evaporated in the Oslo crystallizer in ammonium sulfate crystallization section [a] and was condensed and discharged as condensate [205]. The temperature in Oslo crystallizer in ammonium sulfate crystallization section [a] was maintained at about 70° C. The concentration of organic components and the concentration of ammonium sulfate in the Oslo crystallizer in ammonium sulfate crystallization section [a] were so high that a three-phase system was formed: a liquid oily phase with a high content of organic components, a liquid aqueous ammonium sulfate comprising phase and a solid phase comprising ammonium sulfate crystals.

A mixture of mainly the liquid oily phase with a high content of organic components, and the liquid aqueous ammonium sulfate comprising phase [206] was discharged as a side-stream from the Oslo crystallizer in ammonium sulfate crystallization section [a] and charged to a separation vessel in liquid-liquid separation section [b]. This mixture did contain small amounts of the fine ammonium sulfate crystals. The weight to weight ratio of the liquid oily phase with a high content of organic components, and the liquid aqueous ammonium sulfate comprising phase in mixture [206] was on average about 1:8. In the separation vessel in liquid-liquid separation section [b] a phase separation was observed, whereby a liquid oily layer was on top. The average residence time in the separation vessel in liquid-liquid separation section [b] was about 1 hour. The top layer was discharged from the separation vessel in liquid-liquid separation section [b] as liquid oily phase with a high content of organic components [208]. A typical composition of this liquid oily phase [208] was: organic components content (expressed as COD): 1000 to 1500 gram/kg liquid oily phase; ε-caprolactam: 3 to 6 wt. %; ammonium sulfate: 12 to 20 wt. %; water 18 to 30 wt. %. The density (measured at a temperature of 25° C.) of this liquid oily phase [208] ranged from 1150 to 1220 kg/$m^3$ liquid oily phase. The bottom layer, an aqueous ammonium sulfate comprising phase was discharged from the separation vessel in liquid-liquid separation section [b] as aqueous phase [207] and was charged to the Oslo crystallizer in ammonium sulfate crystallization section [a].

An ammonium sulfate containing slurry [209] was discharged from the Oslo crystallizer in ammonium sulfate crystallization section [a] and was charged to a continuous centrifuge in liquid-solid separation section [c], in which ammonium sulfate crystals were separated off. The ammonium sulfate crystals were washed with water before being discharged as washed wet ammonium sulfate crystals [211]. The remainder, an aqueous ammonium sulfate comprising phase or a diluted ammonium sulfate slurry [210] was recharged to the Oslo crystallizer in ammonium sulfate crystallization section [a].

The washed wet ammonium sulfate crystals [211] and water [212] were charged to a stirred vessel in ammonium sulfate dissolution section [e]. An aqueous flow of ammonium sulfate phase [213], that contained about 40 wt. % ammonium sulfate, was discharged from the stirred vessel in ammonium sulfate dissolution section [e]. The aqueous flow of ammonium sulfate phase [213] was charged as feed to evaporative type crystallization section [I].

The quality of both the first grade ε-caprolactam [28] and the dried ammonium sulfate crystals [21] produced in Example 1 were equal to those in Comparative Example 1.

However, in Example 1, the amount of dried ammonium sulfate crystals [21] per ton of produced ε-caprolactam was increased by about 3 wt. % compared to Comparative Example 1.

The comparison of the results of Example 1 to those of Comparative Example 1 show that the disposal of phases comprising aqueous ammonium sulfate and organic components can be avoided without negative effects on the quantity and quality of the obtained products ε-caprolactam and ammonium sulfate. Further, Example 1 shows that 3% more high grade crystalline ammonium sulfate is obtained. And in addition, a liquid oily phase is obtained that can be incinerated without addition of extra fuel. All these advantages allow the generation of more valuable products, lower costs related to disposal of by-products, and less impact on the environment. As an overall result, Example 1 reduced the overall carbon footprint of the process to produce polyamide 6 and its coproducts.

The invention claimed is:

1. A method for the production of crystalline ammonium sulfate in an industrial scale plant, wherein the plant comprises a Beckmann rearrangement reaction section,
a neutralization section,
a first liquid-liquid separation section,
a first and a second extraction section,
a first solvent recovery section,
a first and a second evaporative crystallization section, and
a first liquid-solid separation section;

wherein the method comprises the steps of:

a) charging components
(i) oleum; and
(ii) cyclohexanone oxime to the Beckmann rearrangement reaction section and reacting the oleum and cyclohexanone oxime to form a mixture comprising ε-caprolactam;

b) discharging the mixture comprising ε-caprolactam from the Beckmann rearrangement reaction section to the neutralization section;

c) adding ammonia and water to the mixture comprising ε-caprolactam in the neutralization section to form a neutralized Beckmann rearrangement mixture that comprises a first aqueous ammonium sulfate phase and an aqueous ε-caprolactam phase, both of which comprise organic components as impurities;

d) separating the first aqueous ammonium sulfate phase and the aqueous ε-caprolactam phase formed in the neutralization section in the first liquid-liquid separation section to form a separated first aqueous ammonium sulfate phase and a separated aqueous ε-caprolactam phase, wherein the separated first aqueous ammonium sulfate phase comprises residual ε-caprolactam;

e) treating the separated first aqueous ammonium sulfate phase of step d) by e.1) extracting the separated first aqueous ammonium sulfate phase with a first organic solvent in the first extraction section to form a phase comprising first organic solvent and residual ε-caprolactam, and an extracted first aqueous ammonium sulfate phase;

e.2) charging the extracted first aqueous ammonium sulfate phase to the first solvent recovery section to recover first organic solvent and form a recovered first aqueous ammonium sulfate phase;

e.3) charging the recovered first aqueous ammonium sulfate phase to the first evaporative crystallization section and performing evaporative crystallization to form a slurry comprising crystalline ammonium sulfate and a mother liquor in the first evaporative crystallization section, wherein the mother liquor is an aqueous ammonium sulfate phase enriched in organic components compared to the recovered first aqueous ammonium sulfate phase;

e.4) discharging a fraction of the mother liquor from the first evaporative crystallization section; and e.5) discharging the slurry from the first evaporative crystallization section and charging it to the first liquid-solid separation section to recover crystalline ammonium sulfate;

f) treating the separated aqueous ε-caprolactam phase of step d) by f.1) extracting the separated aqueous ε-caprolactam phase in the second extraction section with a second organic solvent to form a phase comprising second organic solvent and ε-caprolactam, and a second aqueous ammonium sulfate phase comprising organic components, wherein the organic components of the second aqueous ammonium sulfate phase comprise second organic solvent; and f.2) recovering second organic solvent from the second aqueous ammonium sulfate phase comprising organic components to form a recovered second aqueous ammonium sulfate phase;

g) charging the second evaporative crystallization section with (i) the fraction of the mother liquor that is discharged from the first evaporative crystallization section in step e.4); and/or (ii) the recovered second aqueous ammonium sulfate phase of step f.2), performing evaporative crystallization on the mother liquor and/or the recovered second aqueous ammonium sulfate phase to form a three-phase system comprising:

(1) a liquid oily phase comprising organic components;
(2) a crystalline ammonium sulfate phase; and
(3) a liquid aqueous ammonium sulfate comprising phase; and (iii) recovering at least the liquid oily phase from the three-phase system.

2. The method according to claim 1, wherein the liquid oily phase comprises between 0.5 and 25 wt. % of ε-caprolactam;
comprises 1 to 30 wt. % of ammonium sulfate; and
has an organic components content from 500 to 2000 gram Chemical Oxygen Demand (COD)/kg of the liquid oily phase.

3. The method according to claim 1, wherein the liquid oily phase is used as fuel in an incineration device.

4. The method according to claim 1, further comprising removing water from the second aqueous ammonium sulfate phase prior to step g).

5. The method according to claim 1, wherein the recovery of crystalline ammonium sulfate from the first evaporative crystallization section in step e.5) comprises the steps of e.5.1) discharging from the first evaporative crystallization section the slurry and charging the slurry to the first liquid-solid separation section; and e.5.2) discharging crystalline ammonium sulfate from the first liquid-solid separation section and charging the crystalline ammonium sulfate to a first drying section to form dried crystalline ammonium sulfate.

6. The method according to claim 1, wherein the plant comprises a second liquid-liquid separation section and a second liquid-solid separation section, and wherein the recovery of at least the liquid oily phase in step (iii) further comprises the steps of:

(iii.1) discharging from the second evaporative crystallization section a mixture comprising the liquid oily phase and the liquid aqueous ammonium sulfate comprising phase, and charging the mixture comprising the liquid oily phase and the liquid aqueous ammonium sulfate comprising phase to the second liquid-liquid separation section to form a separated liquid oily phase and a separated liquid aqueous ammonium sulfate comprising phase;

(iii.2) recovering the separated liquid oily phase and the separated liquid aqueous ammonium sulfate comprising phase from the second liquid-liquid separation section; and (iii.3) discharging from the second evaporative crystallization section a second slurry formed in the second evaporative crystallization section, wherein the second slurry comprises the crystalline ammonium sulfate phase and the liquid aqueous ammonium sulfate comprising phase, and charging the second slurry to the second liquid-solid separation section to recover crystalline ammonium sulfate and liquid aqueous ammonium sulfate phase.

7. The method according to claim 6, further comprising charging

The separated liquid aqueous ammonium sulfate comprising phase recovered from the second liquid-liquid separation section in step (iii.2) and/or the liquid aqueous ammonium sulfate phase recovered from the second liquid-solid separation section in step (iii.3), to the second evaporative crystallization section.

8. The method according to claim 6, further comprising washing the crystalline ammonium sulfate that is discharged from the second liquid-solid separation section in step (iii.3) with an aqueous solution.

9. The method according to claim 6, wherein a weight ratio of the liquid oily phase to the liquid aqueous ammonium sulfate comprising phase of the mixture comprising the liquid oily phase and the liquid aqueous ammonium sulfate comprising phase that is discharged from the second evaporative crystallization section and charged to the second liquid-liquid separation section in step (iii.1) is less than 1.

10. The method according to claim 1, further comprising charging crystalline ammonium sulfate recovered from the three-phase system in step g) to a dissolving section;

dissolving the crystalline ammonium sulfate in water in the dissolving section to form an aqueous ammonium sulfate comprising phase; and charging the aqueous ammonium sulfate comprising phase to the first evaporative crystallization section.

11. The method according to claim 1, wherein the first organic solvent used in the first extraction section and the second organic solvent used in the second extraction section are independently selected from the group consisting of benzene, toluene, trichloroethylene, alcohols, and mixtures thereof.

* * * * *